United States Patent [19]
Abrahamsson

[11] Patent Number: 5,693,853
[45] Date of Patent: Dec. 2, 1997

[54] PHOSGENATION METHOD

[75] Inventor: Sören Abrahamsson, Karlskoga, Sweden

[73] Assignee: Chematur Engineering AB, Karlskoga, Sweden

[21] Appl. No.: 557,566

[22] Filed: Nov. 14, 1995

[30] Foreign Application Priority Data

Nov. 15, 1994 [SE] Sweden ................................. 9403929

[51] Int. Cl.⁶ ............................................. C07C 263/00
[52] U.S. Cl. .............................................. 560/347
[58] Field of Search ................................. 560/347

[56] References Cited

U.S. PATENT DOCUMENTS

| | | | |
|---|---|---|---|
| 3,912,600 | 10/1975 | Hatfield, Jr. et al. | 203/73 |
| 4,014,914 | 3/1977 | Pistor et al. | 260/453 PH |
| 4,251,457 | 2/1981 | Kondratenko et al. | 260/544 |

FOREIGN PATENT DOCUMENTS 55-162415   12/1980   Japan.

*Primary Examiner*—Samuel Barts
*Attorney, Agent, or Firm*—Sughrue, Mion, Zinn, Macpeak & Seas, PLLC

[57] ABSTRACT

A method of phosgenation while using carbonyl chloride produced from chlorine and contaminated carbon monoxide. The obtained contaminated carbonyl chloride is purified prior to being delivered to the phosgenation process. The carbonyl chloride is purified by absorption in a solvent and the obtained carbonyl chloride solution is used for the phosgenation reaction. The carbonyl chloride is conveniently purified in an absorption column which is also used to recover carbonyl chloride from waste gases deriving from the phosgenation process, wherein the solution of fresh and recovered carbonyl chloride is delivered commonly to the phosgenation process.

5 Claims, 3 Drawing Sheets

PHOSGENATION METHOD

The present invention relates to a method for application in phosgenation processes with the use of carbonyl chloride which is produced from chlorine and contaminated carbon monoxide, such as crude gas containing nitrogen, carbon dioxide and hydrogen.

Carbonyl chloride, known commonly as phosgene, intended for industrial scale phosgenation is normally produced by passing carbon monoxide and chlorine in gas phase over a bed of activated carbon. The carbonyl chloride obtained can be used to phosgenate amines to isocynates. The largest single consumption of carbonyl chloride on a world wide basis is found in the production of toluene diisocyanate, TDI, methylene diphenyldiisocyanate, MDI, and polymer-MDI, i.e. MDI with more than two phenyl rings, and polycarbonate. Carbonyl chloride is also used in the production of other types of isocynates for use in the manufacture of polyurethanes, such as aliphatic isocyanates, etc., and also for the production of certain herbicides and pesticides.

Typical raw materials used to produce carbon monoxide are natural gas (methane), coal, coke and in some cases methanol. Normally, water vapour is passed over a catalyst to convert to a gaseous mixture consisting of hydrogen gas, carbon monoxide, carbon dioxide and water. The hydrogen gas and carbon monoxide are separated and purified. The carbon monoxide obtained will typically have a purity of about 98%.

Contaminants present in the carbon monoxide used as crude material will also be present in the carbonyl chloride produced. The inert compounds, such as nitrogen gas and carbon dioxide, will be present in essentially the same concentrations as they were present in the carbon monoxide. Certain contaminants will react over the carbon bed. For instance, methane is converted to carbon tetrachloride and hydrochloric acid.

Carbon monoxide is normally used in an excess of 1–5% in the synthesis of carbonyl chloride, in order to keep unreacted chlorine at an acceptable low level.

For an isocyanate project, such as a TDI plant or an MDI plant, the investment costs and operating cost of the carbon monoxide production is highly significant to the total economy of the project.

Hydrochloric acid is formed in the phosgenation process and must be removed from the reactor. This hydrochloric acid normally leaves the reactor together with carbonyl chloride, in larger or smaller quantities. The phosgenation reactor is therefore normally provided with a carbonyl chloride recovery system. This system includes an absorption column which operates with an organic solvent that dissolves the carbonyl chloride while allowing the hydrochloric acid and the inert gases to pass through the column. The solvent containing dissolved carbonyl chloride is then returned to the phosgenation reaction process. A similar method is described, for instance, in DE-C2-2 926 007, in which the reaction product benzoyl chloride is used to dissolve the carbonyl chloride introduced into the process. This is analogous with the formation of the phosgenation process in the production of TDI and MDI with regard to dissolving carbonyl chloride present in the waste gases in a solvent and returning the carbonyl chloride to the phosgenation process.

The main object of the present invention is to enable phosgenation processes to be carried out with the aid of carbonyl chloride that has been produced from inexpensive, contaminated carbon monoxide, for instance from crude gas obtained as a process by-product. In order to achieve this, it is necessary to be able to purify the carbonyl chloride produced prior to delivering it to the phosgenation process.

Hitherto, the carbonyl chloride has been purified by liquefaction of the carbonyl chloride, using compression and cooling techniques. The non-condensible gases are ventilated together with a certain amount of carbonyl chloride and passed to an alkali scrubber, whereafter the liquid carbonyl chloride can be used in its liquid state or may be vapourized prior to its use in the phosgenation process.

For safety reasons, it is Applicant's philosophy never to liquify carbonyl chloride and never to store liquid carbonyl chloride, and consequently the liquefaction method of purifying Carbonyl chloride is not acceptable to Applicant.

The present invention is based on the concept of purifying lean contaminated carbonyl chloride gas for use in the phosgenation process in accordance with the same principle as that used to recover carbonyl chloride from the process waste gases.

Accordingly, the present invention relates to a method of the kind defined in the introductory paragraph of this document which is primarily characterized by purifying the obtained contaminated carbonyl chloride by absorption in a solvent, and by using the thus obtained carbonyl chloride solution to effect the phosgenation reaction.

This method enables the carbonyl chloride to be purified effectively in the absence of liquefaction.

According to a particularly preferred embodiment of the method, the absorption of fresh, contaminated carbonyl chloride is effected in at least one absorption column or tower, which is also used for recovering carbonyl chloride from the waste gases generated in the phosgenation process, and the solution of fresh and recovered carbonyl chloride is delivered commonly to the phosgenation process.

This method thus requires no additional purification process steps, because purification is effected simultaneously with the recovery process. The inert substances, essentially nitrogen and carbon dioxide, leave the absorber in a gaseous state, together with surplus carbon monoxide and hydrochloric acid.

The carbon monoxide source may be a gas obtained as a by-product from steel works using oxygen blast furnaces. The degree of purity may typically lie within the range of 40–95 percent by volume, which results in a corresponding degree of purity of the produced, lean carbonyl chloride.

The absorber will conveniently comprise an absorption column and both the fresh, contaminated carbonyl chloride and the waste gases from the phosgenation process are delivered to the bottom of the column. The column may have any form of gas-liquid contact apparatus, such as packed towers, towers with structured packing or plate towers equipped with sieving plates, valve plates or frusto-conical plates. The solvent used in the absorption column or tower may be ODCB (orthodichlorobenzene), an isomer mixture of dichlorobenzenes, monochlorobenzene, toluene or some other suitable solvent.

The working pressure in the absorber may be in the range of from atmospheric pressure to a pressure of about 20 bars. The process temperature may lie within the range of from 2° C. above the freezing point of the solvent to about 100° C.

The method can be applied in conjunction with phosgenation in the manufacture of such products as TDA (toluene diamine), MTD (metatoluene diamine), MDA (methylenediphenyl diamine), PMA (polymethylene polyphenyl polyamine) or other aliphatic or aromatic amines.

With the intention of illustrating the principle of the present invention and making the differences between the inventive method and the known technique apparent, reference is also made to the accompanying drawing in which

BRIEF DESCRIPTION OF DRAWINGS

In FIG. 1, the process of phosgene synthesis is effected in accordance with block 1 with the aid of highly pure carbon monoxide, purity about 98%, and chlorine gas, wherein the obtained phosgene can be supplied to the phosgenation stage according to block 2 without being purified. The phosgene is recovered in accordance with block 3, by dissolving the phosgene in a solvent, such as ODCB. The solvent and the dissolved phosgene are then fed to the phosgenation process in accordance with block 2, whereas the hydrochloric acid formed in the process is discharged from the system.

FIG. 2 illustrates another known process, in which contaminated carbon monoxide is used for the phosgene synthesis in accordance with block 1. The phosgene produced is then purified in accordance with block 4, by liquefaction of the phosgene, using compression and cooling techniques to this end. The non-condensible gases are evacuated together with some phosgene and passed to an alkali scrubber, whereafter phosgene in either a liquid state or in a re-vapourized state is passed to the phosgenation process in accordance with block 2. This method involves the handling of liquid phosgene, a process which the present Applicant finds highly unacceptable.

FIG. 3 illustrates a process according to the present invention. Contaminated carbon monoxide, for instance carbon monoxide present in crude gas obtained as a process by-product, is delivered to the phosgene synthesis stage in accordance with block 1. This synthesis process results in contaminated phosgene, which instead of being passed directly to the phosgenation step is passed to the phosgene recovery stage in accordance with block 3. As with the process illustrated in FIG. 1, the hydrochloric acid which leaves the phosgenation stage 2 and which is contaminated with a certain amount of phosgene is also delivered to the phosgene recovery stage in accordance with block 3. In block 3, both the phosgene from stage 1 and the phosgene from stage 2 are dissolved in solvent, e.g. ODCB. This phosgene bearing solvent is passed to the phosgenation stage in accordance with block 2, whereas phosgene-free hydrochloric acid is discharged from the system in accordance with block 3, together with other contaminants.

Figure 1:
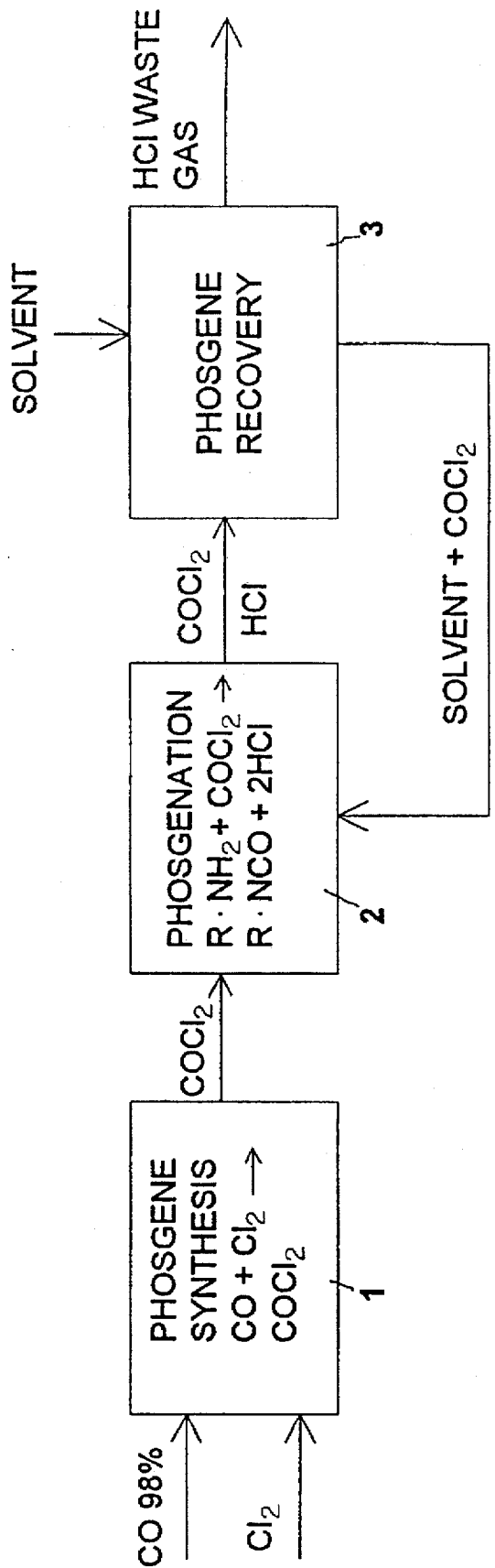
FIGS. 1 and 2 are block schematics which illustrate the method steps of two known processes.
Figure 2:
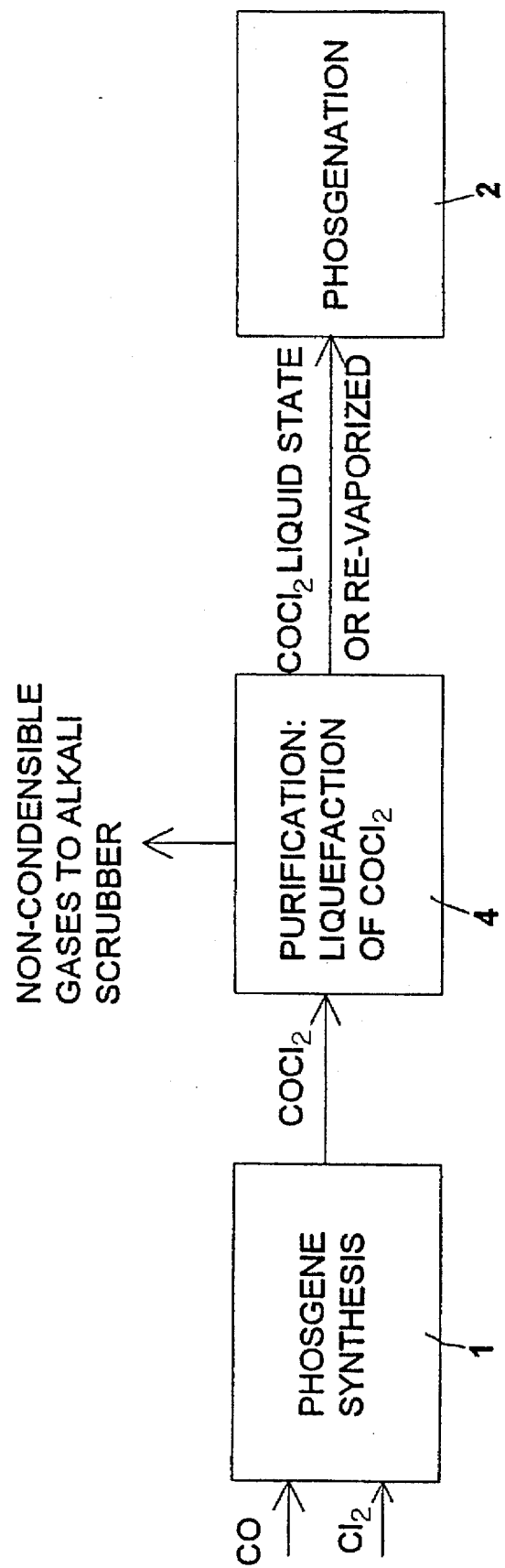
Figure 3:
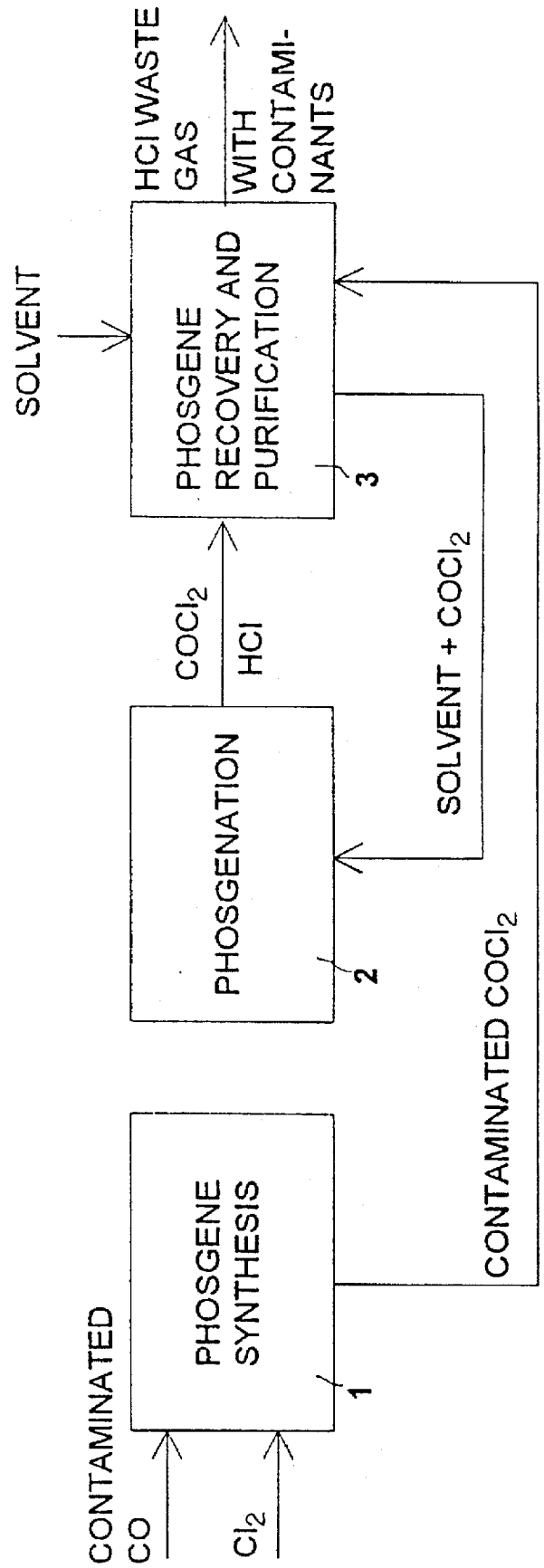
FIG. 3 is a block schematic illustrating the method steps of an inventive process.

This method, which involves the use of contaminated carbon monoxide, is essentially as easy to carry out as the method illustrated in FIG. 1, with the exception that this latter method requires the use of pure carbon monoxide. The inventive method requires no separate purification stage with the subsequent need to handle liquid phosgene, in contradistinction to the method illustrated in FIG. 2, because the contaminants in the crude gas are removed in the recovery stage, this stage being nevertheless necessary to recover the phosgene which leaves the phosgenation stage together with hydrochloric acid.

Planning of a plant for the manufacture of TDI with the aid of the present invention will now be described by way of example.

The TDI plant is positioned in the vicinity of a steel mill to which purchased oxygen gas is delivered through an oxygen-gas delivery pipeline and which pipes contaminated CO to the TDI plant at a concentration of 65–77 percent by volume.

The diluted carbon monoxide is used to produce contaminated carbonyl chloride ($COCl_2$) in accordance with the present invention, this contaminated carbonyl chloride being purified in the same recovery column as that normally used to recover $COCl_2$ from Hcl in the waste gases from the phosgenation stage.

The solvent used in the TDI plant is ODCB, which is also the solvent used in the recovery stage. The phosgene absorber is in the form of a valve plate column and is constructed for double capacity and uses twice as much ODCB as a corresponding plant that operates with pure (98%) carbon monoxide. A downstream ODCB recovery system requires a capacity which is 17% larger than when pure carbon monoxide is used.

The advantage with this system is that no extra process step is required for purification purposes, and that the contaminated CO by-product from the steel mill can be utilized, which contributes towards improving the economy of both the steel mill and the TDI plant. The process does not influence the quality of TDI in a negative sense. The slight increase in the amount of ODCB required (+17%) contributes towards a slight improvement in the yield from the phosgenation stage.

I claim:

1. A method of phosgenation with the aid of carbonyl chloride produced from chlorine and contaminated carbon monoxide, wherein the produced carbonyl chloride with contaminants is purified; and the purified carbonyl chloride is used to effect the phosgenation reaction;

comprising absorbing fresh, contaminated carbonyl chloride in a solvent in at least one absorption column which is also used to recover carbonyl chloride from waste gases deriving from the phosgenation process to effect purification of the fresh, contaminated carbonyl chloride simultaneously with recovery of carbonyl chloride from the waste gases and form a solution of fresh and recovered carbonyl chloride; and delivering the solution of fresh and recovered carbonyl chloride from the absorption column commonly to the phosgenation process.

2. A method according to claim 1, using ODCB (orthodichlorobenzene), an isomer mixture of dichlorobenzenes, monochlorobenzene or toluene as said solvent.

3. A method according to claim 1, using as crude material carbon monoxide having a degree of purity in the range of 40–95 percent by volume, which results in a corresponding degree of purity of the diluted carbonyl chloride gas obtained.

4. A method according to claim 1, wherein the absorber is operated at a pressure within the range of from atmospheric pressure to a pressure of 20 bars.

5. A method according to claim 1, wherein the working temperature is within the range of from 2° C. above the freezing point of the solvent used to a temperature of about 100° C.

* * * * *